| United States Patent [19] | [11] | 4,124,749 |
|---|---|---|
| Aharoni | [45] | Nov. 7, 1978 |

[54] ARYL MERCURY CONTAINING POLYMERS

[75] Inventor: Shaul M. Aharoni, Morris Plains, N.J.

[73] Assignee: Allied Chemical Corporation, Morristown, N.J.

[21] Appl. No.: 775,345

[22] Filed: Mar. 7, 1977

[51] Int. Cl.² .............................................. C08F 8/42
[52] U.S. Cl. ........................................ 526/15; 526/16; 526/30; 526/46; 526/48.1; 526/55
[58] Field of Search .................... 526/48.1, 46, 30, 15, 526/16

[56] References Cited

U.S. PATENT DOCUMENTS

| 3,201,376 | 8/1965 | Osborn et al. ...................... 526/48.1 |
| 3,267,083 | 8/1966 | Imhof ................................. 526/48.1 |
| 3,367,898 | 2/1968 | Cadmus ............................. 526/48.1 |

*Primary Examiner*—William F. Hamrock
*Attorney, Agent, or Firm*—Robert J. North; Gerhard H. Fuchs

[57] ABSTRACT

Production of aryl mercury containing polymers is described, which are useful as fungicides in paints and coatings. Certain of the aryl mercury containing polymers are novel.

18 Claims, No Drawings

ARYL MERCURY CONTAINING POLYMERS

BACKGROUND OF THE INVENTION

1. Field of the Invention

This invention relates to production of aryl mercury containing polymers useful as fungicides.

2. Brief Description of the Prior Art

Aryl mercury containing compounds are well known in the art as exhibiting biological activity as fungicides, mildewcides, and bacteriocides.

U.S. Pat. No. 3,367,898 (1968) discloses a process for protecting articles against attack by fungus and mildew by the use of paint compositions containing a copolymer of phenyl mercuric acrylate or phenyl mercuric methacrylate. The copolymers are prepared by copolymerizing phenyl mercuric acrylate monomer or phenyl mercuric methyacrylate monomer with vinyl acrylate or an acrylate monomer such as ethyl acrylate. However, this process is limited to those polymers which can be formed from aryl mercury containing acrylic monomers and is unsuitable for those polymers requiring condensation polymerization.

Phenylmercuric hydroxide is also known as a catalyst in the esterification of terephthalic acid with ethylene glycol, as disclosed in French Pat. No. 1,544,484 (1968), the ester being polymerized in the presence of $Sb_2O_3$ or $Sb_2S_3$ to form polyethylene terephthalate. However, the prior art does not provide a method for producing polyethylene terephthalate containing arylmercurioxycarbonyl groups since at the high polymerization temperature recited, i.e. 282° C., the arylmercurioxycarbonyl radical is unstable.

Russian Pat. No. 181,277 (1966) discloses styrene polymers containing phenyl mercury groups which are useful as anion exchange reagents. However, the polymers are formed by reacting the aromatic styrene portion of the polymer with mercuric acetate, wherein the structure of the resulting mercury containing group is that of an acetoxymercuriphenyl radical,

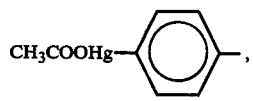

rather than the highly fungicidally active phenylmercurioxycarbonyl radical,

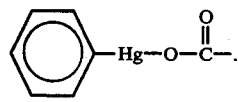

Ethylene-maleic anhydride copolymer has been reacted with p-(acetoxymercuri)aniline to form a substrate useful in the determination of sulfur compounds, as described in Arch, Biochem. Biophys. 121(1), 67–72 (1967), but the resulting water insoluble copolymer also contains the acetoxymercuriphenyl radical.

Therefore, there is a need in the art for a process, which the prior art does not provide, for preparing a wide range of polymers containing an arylmercurioxycarbonyl radical, including those polymers requiring high polymerization temperatures.

SUMMARY

In accordance with this invention, there is provided a method of producing a polymeric composition containing an arylmercurioxycarbonyl radical which comprises reacting a polymer containing a pendant organic radical selected from the group consisting of —COOH, —COOM, —CO—O—CO—, —COOR and mixtures thereof, wherein R is alkyl and M is a metal or ammonium cation, said polymer being essentially free of affixed alcoholic —OH groups, with an aryl mercury compound of the formula:

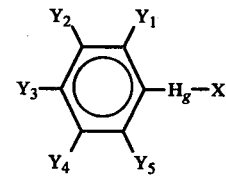

wherein the substituents $Y_1$ to $Y_5$ can be the same or different and are independently selected from the group consisting of hydrogen, halogen, alkyl, alkoxy, phenyl, nitro and alkylthio and X is selected from the group consisting of halogen, hydroxy and alkylcarbonyloxy, in the presence of a solvent for the polymer, at a temperature of 140° to 180° C.

Novel polymeric compositions are also provided comprising a polymer selected from the group consisting of homopolymers and copolymers of (a) condensation products of dicarboxylic acids, their anhydrides, esters, acid halides and mixtures thereof with diols or diamines;

(b) maleic anhydride; and (c) amino acids, said polymer having incorporated therein an arylmercurioxycarbonyl radical.

DETAILED DESCRIPTION

This invention involves a method for preparing aryl mercury containing polymers useful as fungicides in paints and coatings. Aryl mercury compounds are known to be highly effective antiseptic and fungicidal agents, and polymers formed from acrylate monomers containing an arylmercurioxycarbonyl radical are known to be effective fungicidal agents in paint formulations. However, the prior art does not provide a method for producing a wide range of polymers containing the arylmercurioxycarbonyl radical, including polymers requiring high polymerization temperatures, in which polymers can be directly reacted with an aryl mercury compound.

It has been found that a wide range of polymers containing an arylmercurioxycarbonyl radical can be directly prepared by reacting a polymer containing a pendant organic radical selected from the group consisting of —COOH, —COOM, —CO—O—CO—, —COOR and mixtures thereof, wherein R is alkyl and M is a metal or ammonium cation, said polymer being essentially free of affixed alcoholic —OH groups, with an aryl mercury compound of the formula:

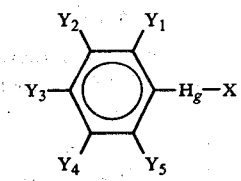

wherein the substituents $Y_1$ to $Y_5$ can be the same or different and are independently selected from the group consisting of hydrogen, halogen, alkyl, alkoxy, phenyl, nitro and alkylthio and X is selected from the group consisting of halogen, hydroxy, and alkylcarbonyloxy, in the presence of a solvent for the polymer, at a temperature of 140° to 180° C.

The method of preparation of these polymers initially involves dissolving the polymer containing pendant carboxylic acid functionality in an inert solvent, such as nitrobenzene. The requisite amount of aryl mercury compound, such as phenylmercuric hydroxide, acetate or chloride, is then added at a temperature of 140° C. to 180° C. The reaction between the aryl mercury compound and the carboxylic acid, acid salt, anhydride, ester or acid chloride affixed to the polymer is complete at this temperature within a relatively short time. The aryl mercury containing polymer is then poured into a nonsolvent for the polymer such as methanol and washed several times to remove residual solvent and then dried. The arylmercurioxycarbonyl bonds present in the polymer tend to decompose above 180° C., and thus the polymers should not be exposed to temperatures higher than 180° C. during preparation or subsequent end use. However, the polymers are readily adaptable as components in paint applications since the required operations are normally carried out at room temperature which is well below the decomposition temperature of the arylmercurioxycarbonyl radical.

The polymers which are applicable in the instant invention comprise polymers containing a pendant organic radical selected from the group consisting of —COOH, —COOM, —CO—O—CO—, —COOR and mixtures thereof, wherein R is alkyl and M is a metal or ammonium cation, wherein the polymer is essentially free of affixed alcoholic —OH groups. In general, any polymer that contains these characteristics is applicable in the invention and the scope of the the invention is intended to include those polymers which embody those characteristics.

It has been found that polymers containing affixed alcoholic —OH groups, i.e. hydroxy groups attached to alkyl carbon atoms such as —CH$_2$OH, will adversely affect the formation of arylmercurioxycarbonyl radicals, by decomposing the aryl mercury compound to elemental mercury and other organic side products. Thus, only up to about one percent of alcoholic —OH groups can be tolerated in the polymers of this invention. Polymers having up to such amount of alcoholic —OH groups are designated herein as "essentially free" of alcoholic —OH groups. It is preferred to use polymers having less than 0.1 percent of alcoholic —OH groups. In a condensation polymer, such as polyethylene terephthalate, which is formed by the condensation of terephthalic acid, ester or acid chloride with ethylene glycol, an excess of the terephthalate reagent must be used to insure that the end groups of the polymer chain are not alcoholic hydroxyl, but instead contain carboxylic acid functionality. This proviso applies to all polymers in this invention made from the condensation involving a diol.

The term "pendant" as used herein refers to the carboxylic acid, salt, anhydride and ester radicals which are affixed to the polymer chain, either along the polymer chain such as the methylcarboxylate radical, —COOCH$_3$ in polymethylacrylate, or on the ends of the polymer chain, such as end methylcarboxylate radicals in polyethylene terephthalate, and are available for reaction with an aryl mercury compound. In the case of the anhydride radical, —CO—O—CO—, the formula indicates that it is attached to the polymer chain at two points, such as in polymaleic anhydride or ethylenemaleic anhydride copolymer. In general, a particular polymer will only contain one type of pendant carboxylic acid functionality, but may contain more than one type in a mixture, such as a copolymer of acrylic acid and methyl acrylate.

The carboxylic acid salt radical, —COOM, contains either a metal cation or ammonium cation, M, wherein the metal cation is any mono-, di- or trivalent ion capable of salt formation with a carboxylic acid. Representative examples of metal cations that are applicable in the invention are (omitting the valence charges) lithium, sodium, potassium, rubidium, magnesium, calcium, strontium, barium, chromium, molybdenum, iron, cobalt, nickel, silver, cadmium, mercury, aluminum, tin, antimony, bismuth and lead. The two provisos are that the carboxylic acid salt must be soluble in the organic solvent of the reaction as described herein and must undergo reaction with an aryl mercury containing compound. Preferred metal cations are sodium and potassium.

In carboxylic esters, —COOR, where R is alkyl, R may be linear or branched and preferably contains 1 to 4 carbon atoms. Representative examples are methyl, ethyl, propyl, butyl, isobutyl and tertiary butyl. Preferred are the methyl and ethyl radicals.

The arylmercurioxycarbonyl radical is produced by the reaction of an aryl mercury compound as described herein with a polymer containing carboxylic acid functionality such as carboxylic acid, acid salt, anhydride, ester, acid chloride or mixtures thereof.

Esters of polyvinyl alcohol, e.g. polyvinyl acetate, polyvinyl butyrate, are not applicable in the instant invention since the carboxylic acid functionality is not attached to the polymer backbone, and thus, reaction of polymers such as polyvinyl acetate with the aryl mercury compounds of this invention do not produce polymers containing an arylmercurioxycarbonyl radical.

The term "polymer backbone" as used herein refers to the basic "skeleton" of the polymer chain which is formed by the interconnecting "repeating" units of the polymer. The longest continuous line which can be hypothetically drawn through the covalent bonds connecting the atoms in the repeating units of the polymer, without doubling back or returning, will in general consistitute the "backbone" of the polymer, as the term is understood in the art, and will include all the atoms comprising the polymer backbone but will exclude end groups at each end of the backbone, since these ends can be varied without changing the inherent nature of the polymer backbone.

Homopolymers and copolymers of condensation products of dicarboxylic acids, anhydrides, esters, acid halides and mixtures thereof with diols or diamines, wherein the polymer is essentially free of affixed alcoholic —OH groups, are polymers applicable in the instant invention.

Homopolymers and copolymers of polyesters formed from dicarboxylic acids and diols are also an applicable class of polymers.

The dicarboxylic acids used in preparing the polyesters can either be aromatic, aliphatic or cycloaliphatic in nature, and preferably contain from 8 to 16 carbon atoms. Equivalents of the dicarboxylic acids can also be used, namely esters and ester-forming compounds such as acid halides, e.g. acid chloride, and anhydrides. The dicarboxylic acids cannot contain substituents which interfere with the reaction between the polyester and aryl mercury compound, e.g. alcoholic —OH, —SH and —NH$_2$, but can contain substituents such as halogen, e.g. chloro, bromo, fluoro, and iodo, lower alkoxy, such as methoxy, ethoxy and butoxy, and alkyl, such as methyl, ethyl and butyl.

Representative aliphatic and cycloaliphatic dicarboxylic acids which can be used are sebacic acid, 1,3-cyclohexane dicarboxylic acid, 1,4-cyclohexane dicarboxylic acid, adipic acid, glutaric acid, succinic acid, carbonic acid, oxalic acid, azelaic acid, diethylmalonic acid, allylmalonic acid, 4-cyclohexane-1,2-dicarboxylic acid, 2-ethylsuberic acid, 2,2,3,3-tetramethylsuccinic acid, cyclopentanedicarboxylic acid, decahydro-1, 5-naphthalene dicarboxylic acid, 4,4'-bicyclohexyl dicarboxylic acid, decahydro-2,6-naphthalene dicarboxylic acid, 4,4'-methylenebis-(cyclohexane carboxylic acid), 3,4-furan dicarboxylic acid and 1, 1-cyclobutane dicarboxylic acid. The preferred aliphatic dicarboxylic acid is sebacic acid.

Representative aromatic dicarboxylic acids which can be used include phthalic, terephthalic and isophthalic acids, bi-benzoic acid, substituted dicarboxy compounds with two benzene nuclei such as bis(p-carboxyphenyl) methane, 1,5-naphthalene dicarboxylic acid, 2,6-naphthalene dicarboxylic acid, 2,7-naphthalene dicarboxylic acid, phenanthrene dicarboxylic acid, anthracene dicarboxylic acid, 4,4'-sulfonyl dibenzoic acid and 4,4'-benzophenonedicarboxylic acid.

Aromatic dicarboxylic acids are an especially preferred class for preparing the polyesters applicable in this invention. Among the aromatic dicarboxylic acids, those with 8 and 16 carbon atoms are especially preferred, particularly the phenylene dicarboxylic acids, e.g. phthalic, terephthalic and isophthalic acids, their dimethyl ester derivatives and mixtures thereof.

The diols used in preparing the copolyesters can be either high molecular weight glycols or low molecular weight dihydroxy compounds. The high molecular weight glycols refer to polymeric glycol components possessing molecular weights from about 200 to 6,000. These are essentially poly(alkylene oxide) glycols having a carbon to oxygen ratio of about 2.0–4.3. Representative long-chained glycols are poly(ethylene oxide) glycol, poly(1,2- and 1,3-propylene oxide) glycol, poly(tetramethylene oxide) glycol and random copolymers of ethylene oxide and 1,2-propylene oxide. Included among the low molecular weight dihydroxy compounds which react to form short-chained ester units are acyclic, alicyclic and aromatic dihydroxy compounds. Preferred are diols with 2–15 carbon atoms such as ethylene, propylene, tetramethylene, pentamethylene, 2,2-dimethyltrimethylene, hexamethylene and decamethylene glycols, dihydroxycyclohexane, cyclohexane dimethanol, resorcinol, di(beta-dihydroxyethyl)resorcinol, hydroquinone, 1,5-dihydroxy naphthalene, etc. Especially preferred are aliphatic diols containing 2 to 8 carbon atoms. Included among the bis-phenols which can be used are bis(p-hydroxy)diphenyl, bis(p-hydroxyphenyl)methane and bis(p-hydroxyphenyl) propane. Equivalent ester-forming derivatives of diols are also useful (e.g. ethylene oxide or ethylene carbonate can be used in place of ethylene glycol).

Examples of some polyesters which can be utilized in the present invention are the halogenated polyesters, where the aromatic rings in the diacid moiety are halogen-containing, the polyester-sulfone copolyesters containing an aromatic sulfone component and the polyester carbonates, preferably in the class prepared by the reaction of polyhydric phenols with phosgene.

Preferred polyesters in the instant invention are the polyalkylene terephthalates, particularly polyethylene terephthalate.

Polyamides are also an applicable class of polymers in the instant invention, with the proviso that they are essentially free of alcoholic hydroxyl groups and preferably of free unreacted amino groups. They are formed by reacting a dicarboxylic acid, anhydride, ester or acid chloride thereof, as mentioned above with a diamine, either aliphatic or aromatic.

Aliphatic diamines that are applicable are the alkyl diamines preferably containing from 2 to 20 carbon atoms, wherein the alkyl group is either branched or linear. The aliphatic diamine can contain other functional groups such as halogen, e.g. chloro, bromo, fluoro and iodo, with the proviso that the group is inert and does not undergo chemical reaction during the polymerization or interfere with the reaction of the aryl mercury compound with the polymer.

Representative examples of aliphatic diamines which can be used are ethylene diamine, 1,2- and 1,3-propylene diamine, 1,4-diaminobutane, 1,10-diaminodecane, 1,12-diaminododecane, 1,7-diaminoheptane, 1,9-diaminononane, 1,8-diaminooctane, 1,5-diaminopentane, 1,2-diamino-2-methylpropane and 1,6-hexanediamine. Preferred among the aliphatic diamines are ethylene diamine and 1,6-hexanediamine.

Aromatic diamines are also applicable in the instant invention, preferably those containing 6 to 14 carbon atoms, and can contain substituents which are inert under the conditions conditions of the reaction such as halogen, e.g. fluoro, chloro, bromo and iodo and lower alkoxy containing 1–4 carbon atoms such as methoxy, ethoxy and butoxy.

Representative examples of aromatic amines are para-, meta- and ortho-phenylenediamine, 2-chloro-p-phenylenediamine, 4-chloro-o-phenylenediamine, 4,4'-diaminostilbene, 2,5-diaminotoluene, 2-methoxy-p-phenylenediamine, 4,4'-methylenedianiline, 1,5-diaminonaphthalene, 1,8-diaminonaphthalene and 9,10-diaminophenanthrene. Preferred among the aromatic diamines is p-phenylenediamine.

Carboxylic acid anhydrides can also be reacted with diols to form polyesters, as for example, dianhydrides, formed from tetracarboxy acids and trianhydrides formed from hexacarboxylic acids. The polyester formed from the reaction between a carboxylic acid anhydride and diol, if an excess of the anhydride is used to insure that the resulting polymer is essentially free of alcoholic —OH hydroxyl groups, will contain ester linkages and free carboxylic acid groups. Thus, the polyester formed can be subsequently reacted with aryl mercury compounds of this invention to form polyesters containing an arylmercurioxycarbonyl radical for each pendant carboxylic acid radical in the polymer.

The carboxylic acid anhydrides applicable in the instant invention preferably contain 10 to 17 carbon atoms, are aromatic, and can contain other substituents which are inert under the conditions of the reaction such as lower alkyl, containing 1 to 4 carbon atoms, lower alkoxy containing 1 to 4 carbon atom, and halogen, e.g. fluoro, chloro, bromo and iodo.

Representative examples of anhydrides are 1,2,4,5-benzenetetracarboxylic acid dianhydride, 3,3',4,4'-benzophenonetetracarboxylic dianhydride, 1,4,,5,8-naphthalenetetracarboxylic dianhydride, 1,2,3,4-benzenetetracarboxylic dianhydride and 1,2,3,4,5,6-hexacarboxylic trianhydride (mellitic trianhydride).

The anhydrides can be reacted with the diols aforementioned to produce polyesters containing pendant carboxylic acid radicals. Preferred among the anhydrides are 1,2,4,5-benzenetetracarboxylic dianydride and mellitic trianhdride.

The anhydrides of this invention can also be reacted with diamines to form polyamides containing pendant carboxylic acid radicals which can subsequently reacted with aryl mercury compounds.

The diamines that can be reacted with the anhydrides are mentioned hereinabove.

Homopolymers and copolymers of maleic anhydride are applicable in the instant invention and include polymaleic anhydride and ethylene-maleic anhydride copolymer.

Amino acids are applicable in the instant invention, preferably containing 4 to 6 carbon atoms, one amino group and two carboxylic acid groups. Representative examples are glutamic acid, aspartic acid, and glutamic-aspartic acid copolymer, and wherein polyglutamic acid is a preferred polymer.

Homopolymers and copolymers of acylic acid, methacrylic acid, and esters thereof are also a class of polymers that are applicable in the instant invention. The esters are generally alkyl, either linear or branched, and contain 1-4 carbon atoms, e.g. methyl, ethyl, isopropyl and butyl.

Representative examples of homopolymers are polyacrylic acid, polymethacrylic acid, polyethylacrlate, polymethyl acrylate, polymethylmethacrylate and polyethylmethacrylate. Representative examples of copolymers are polyacrylic acid-polymethacrylic acid, polymethylacrylate-polymethylmethacrylate and ethylene copolymers thereof.

Preferred among the acrylates are polymethylacrylate and polymethylmethacrylate.

The solvents which are applicable in the instant invention are inert, have good solubility for the polyester and have a boiling point of at least about 140° C., and preferably in the range of 140°-180° C. at atmospheric pressure. However, if one desires, the reaction can be carried out under pressure in an autoclave, thereby allowing the use of a solvent having a lower boiling point. Types of solvents that can be used in the instant invention are mono-, di- and trichlorinated benzenes, monochlorinated naphthalenes, linear and cyclic alkyl sulfones containing 4 to 6 carbon atoms, linear alkyl sulfoxides containing 2 to 4 carbon atoms, cyclic N-alkyl lactams containing 5 to 7 carbon atoms, N,N-dialkyl-formamides containing 3 to 5 carbon atoms, N,N-dialkylacetamides containing 4 to 6 carbon atoms, mono- and dinitrotoluenes, mono- and dinitroxylenes, monochloronitrobenzenes and hexa-alkylphosphoramides containing 6 to 12 carbon atoms.

Representative examples of solvents that can be used are chlorobenzene, para-dichlorobenzene, 1,2,4-trichlorobenzene, 1-chloro and 2-chloronaphthalene, diethyl sulfone, tetramethylene sulfone, dimethyl sulfoxide, N-methylpyrrolidone, N,N-dimethylformamide, N,N-dimethylacetamide, para-nitrotoluene, 2,4-dinitrotoluene, 2,4-dimethylnitrobenzene, nitrobenzene, 1,3,-dinitrobenzene, para-chloronitrobenzene and hexamethylphosphoramide. It is preferred to use nitrobenzene.

The temperature of the reaction is carried out generally at 140° to 180° C., however, it is preferred to use a temperature of about 150° to 175° C.

The time needed for completion of the reaction is usually within a matter of several minutes. Usually 5 to 15 minutes is sufficient, assuming adequate stirring for the complete reaction between the phenyl mercury compound and the polyester.

The aryl mercury compounds which are applicable in the instant invention are given by the following formula:

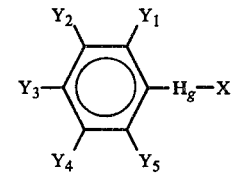

wherein the substituents $Y_1$ to $Y_5$ can be the same or different and are independently selected from the group consisting of hydrogen, halogen, alkyl, alkoxy, phenyl, nitro and alkylthio and X is halogen, hydroxy, and alkylcarbonyloxy.

Substituents $Y_1$ to $Y_5$ include: fluorine, chlorine, bromine and iodine as halogen; linear or branched alkyl, preferably containing 1 to 4 carbon atoms, such as methyl, ethyl, isopropyl, butyl and isobutyl; linear or branched alkoxy, preferably containing 1 to 4 carbon atoms, such as methoxy, ethoxy, isoproxy, butyloxy and tertiary butyloxy; and linear or branched alkylthio, preferably containing 1 to 4 carbon atoms, such as methylthio, ethylthio, isopropylthio, butylthio and tertiary butylthio. Substituent X is hydroxy, halogen, including fluorine, chlorine, bromine and iodine, and alkylcarbonyloxy where alkyl is linear or branched, preferably containing 1-4 carbon atoms, such as methyl.

Representative types of aryl mercury compounds that can be used are shown by the following examples: phenyl mercuric chloride, phenyl mercuric hydroxide, phenyl mercuric acetate, para-chlorophenyl mercuric chloride, para-chlorophenyl mercuric hydroxide, para-bromophenyl mercuric chloride, para-bromophenyl mercuric hydroxide, para-bromophenyl mercuric acetate, para-fluorophenyl mercuric acetate, para-fluorophenyl mercuric hydroxide, para-iodophenyl mercuric hydroxide, 2,4-dimethylphenyl mercuric chloride, para-ethyl mercuric acetate, 2,4-dimethoxyphenyl mercuric propionate, para-butoxy-phenyl mercuric bromide, para-nitrophenyl-mercuric iodide, and 2,4-dimethylthiophenyl-mercuric hydroxide. However, it is preferred to use phenyl mercuric acetate.

The amount of aryl mercury compound used to form the arylmercurioxycarbonyl compounds will vary with the specific polymers of this invention. In general, sufficient aryl mercury compound is used such that at least about 5 numerical percent of the available carbonyl groups present as pendant carboxylic acid, carboxylic ester, or carboxylic anhydride groups are reacted with the aryl mercury containing compounds.

Nonsolvents which can be utilized in the reaction are those which are miscible with the liquid solvent used in the condensation step, but act as a nonsolvent for the desired polymer in order to precipitate it from the reaction solvent. Representative examples of nonsolvents are methanol, ethanol, glycerol and acetone. However, it is preferred to use methanol as the nonsolvent in the reaction.

Methods of isolating the polymer product include conventional techniques such as filtration, wherein the polymer is collected by filtration and then washed with large quantities of the nonsolvent in order to remove all traces of the original solvent and then subsequently dried to remove traces of the nonsolvent.

Not only is the method of preparing the aryl mercury containing polymers the subject of this invention but also certain novel polymeric composition themselves.

The novel polymeric compositions which are included as a subject of this invention are polymers selected from the group consisting of homopolymers and copolymers of (a) condensation products of dicarboxylic acids, their anhydrides, esters, acid halides and mixtures thereof with diols or diamines;
(b) maleic anhydride; and
(c) amino acids, said polymer having incorporated therein an arylmercurioxycarbonyl radical.

The subject homopolymers and copolymers, have all benn hereinabove discussed, including the scope and limitations of the polymers. The incorporated arylmercurioxycarbonly radical is of the formula hereinabove given containing the same scope and limitations.

Preferred compositions are polyethylene terephthalate, styrene-maleic anhydride copolymer and polyglutamic acid having incorporated the phenylmercurioxycarbonyl radical.

Polymers also a subject of this invention are those produced by the direct reaction of an aryl mercury compound and a polymer containing carboxylic acid functionality which are subsequently crosslinked with other compounds, utilizing agents such as an epoxy, e.g., ethylene or propylene oxide, to form a product which then can be used in many applications requiring a hard infusible polymer containing antiseptic and fungicide properties. The subject polymers can be reacted with an epoxy crosslinking agent in the presence of a catalytic amount of peroxide to form the compound directly in the nitrobenzene solvent before isolating the subject polymer.

Polymers included in the scope of those which are crosslinked by reaction with an epoxy crosslinking agent are homopolymers and copolymers of (a) condensation products of dicarboxylic acids, their anhydrides, esters, acid halides and mixtures thereof with diols or diamines;
(b) maleic anhydride;
(c) amino acids; and
(d) acrylic acid, methacrylic acid and esters thereof, said polymer having incorporated therein an arylmercurioxycarbonyl radical.

Preferred compositions are styrene-maleic anhydride copolymer, polyglutamic acid, polymethylmethacrylate and polyethylacrylate all containing a phenylmercurioxycarbonyl radical in which the polymers are reacted with an epoxy crosslinking agent. Typical epoxy crosslinking agents include diglycidyl ether of 2,2-bis(4'-hydroxyphenyl) propane, (bisphenol A) and diglycidyl ether of dihydroxybenzene such as 1,4-dihydroxybenzene.

The following examples are given for illustrative purposes only and are not to be construed as limitations on the scope and the spirit of the instant invention. Parts are by weight unless otherwise indicated.

EXAMPLE 1

A. Polymethylmethacrylate polymer (PMMA), 50 parts, was dissolved with heating in 560 parts nitrobenzene. To the hot solution, which was held at 160° C., there was added 5 parts phenyl mercuric hydroxide, an amount which is 3 weight percent of the stoichiometric amount required to react with all the methacrylate ester residues. The solution was stirred for 10 minutes at 160° C. and then poured into 4000 parts methanol, a nonsolvent for the resulting polymer. The resulting polymer was then filtered, washed several times with methanol and finally dried to yield 52 parts of a solid polymer. Infrared analysis of the resulting polymer revealed a strong carbonyl absorption band at 1535 cm$^{-1}$ ascribed to the formation of the phenylmercurioxycarbonyl radical in addition to the carbonyl absorption band of polymethylmethacrylate at 1730 cm$^{-1}$, also present. Elemental analysis of the resulting polymer revealed the presence of about 10 weight percent of mercury.

B. The procedure of A was repeated, but at a temperature of 180°–185° C., which produced a polyester in which no mercury was found by elemental analysis and no infrared absorption bands were seen at 1535 cm$^{-1}$. This indicated that a phenylmercurioxycarbonyl radical had not been formed under the conditions of the reaction.

C. The procedure of A was repeated, but at a temperature of 135°–140° C., which produced a polyester in which no mercury was found by elemental analysis and no infrared absorption bands were seen at 1535 cm$^{-1}$. This indicated that a phenylmercurioxycarbonyl radical had not been formed under the conditions of the reaction.

EXAMPLE 2

The procedure of Example 1 was repeated, but phenyl mercuric hydroxide was replaced by 5 parts phenyl mercury acetate and the reaction yielded 52.5 parts of resulting polymer. Elemental analysis of the resulting polymer showed mercury present in about 15% by weight of the polymer, and infrared analysis revealed that the substitution of the methyl ester by phenyl mercury was more efficient in the case of the phenyl mercury acetate than in the case of phenyl mercury hydroxide.

EXAMPLE 3

High molecular weight polyethylene terephthalate (PET), 50 parts, was dissolved in 560 parts nitrobenzene at 190° C. The solution was cooled to 170° C. and 5 parts of phenyl mercury hydroxide was added to effect an instantaneous reaction. The remainder of the procedure was conducted the same as in Example 1, yielding 50 parts of resulting polymer, in which some product remained dissolved in the solvent system. Elemental analysis of the resulting polymer showed mercury present in about 4% by weight of the polymer, and molecular weight analysis indicated that the molecular weight of the resulting polymer was lower than that of the starting material. Infrared analysis indicated a carbonyl absorption band at 1730 $cm^{-1}$ indicative of the polyethylene terephthalate and a new carbonyl absorption band at 1635 $cm^{-1}$ ascribed to the phenylmercurioxycarbonyl radical. The higher absorption frequency of the phenylmercurioxycarbonyl radical in PET as contrasted to PMMA is ascribed to the increased aromatic nature of the radical in PET.

EXAMPLE 4

The procedure of Example 1 was followed but the resulting polymer was not isolated. Instead, 20 parts of the diglycidyl ether of bisphenol A was added to the nitrobenzene solution of resulting polymer and the mixture was stirred and heated for about 6 hours at 120°–150° C. About 70 parts of an insoluble crosslinked polymer product was formed.

We claim:

1. A method of producing a solid polymeric composition containing an arylmercurioxycarbonyl radical which comprises reacting in solution a polymer selected from the group consisting of homopolymers and copolymers of maleic anhydride and acrylic acid, methacrylic acid and esters thereof, said polymer containing a pendant organic radical selected from the group consisting of —COOH, —COOM, —CO—O—CO—, —COOR and mixtures thereof, wherein R is alkyl and M is a metal or ammonium cation, said polymer being essentially free of affixed alcoholic —OH groups, with an aryl mercury compound of the formula:

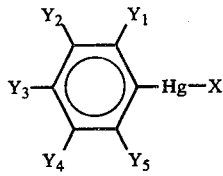

wherein the substituents $Y_1$ to $Y_5$ can be the same or different and are independently selected from the group consisting of hydrogen, halogen, alkyl, alkoxy, phenyl, nitro and alkylthio and X is selected from the group consisting of halogen, hydroxy and alkylcarbonyloxy, in the presence of a solvent for the polymer, at a temperature of 140° to 180° C.

2. The method of claim 1 wherein the temperature is about 150° to 175° C.

3. The method of claim 1 wherein R is alkyl containing 1 to 4 carbon atoms and M is selected from the group consisting of ammonium, sodium and potassium.

4. The method of claim 1 wherein substituents $Y_1$ to $Y_5$ are independently selected from the group consisting of hydrogen fluorine, chlorine, bromine, iodine, alkyl containing 1-4 carbon atoms, alkoxy containing 1-4 carbon atoms and alkylthio containing 1-4 carbon atoms, and X is selected from the group consisting of fluorine, chlorine, bromine, iodine, hydroxy and alkylcarbonyloxy where alkyl contains 1 to 4 carbon atoms.

5. The method of claim 4 wherein the aryl mercury compound is phenyl mercuric acetate.

6. The method of claim 1 wherein the solvent for the polymer is selected from the group consisting of mono-, di-, and trichlorinated benzenes, monochlorinated naphthalenes, linear and cyclic alkyl sulfones containing 4 to 6 carbon atoms, linear alkyl sulfoxides containing 2 to 4 carbon atoms, cyclic N-alkyl lactams containing 5 to 7 carbon atoms, N,N-dialkylformamides containing 3 to 5 carbon atoms, N,N-dialkylacetamides containing 4 to 6 carbon atoms, mono- and dinitrobenzenes, mono- and dinitrotoluenes, mononitroxylenes, monochloronitrobenzenes and hexa-alkylphosphoramides containing 6 to 12 carbon atoms.

7. The method of claim 6 wherein the solvent is nitrobenzene.

8. The method of claim 3 wherein the polymer is selected from the group consisting of homopolymers and copolymers of polyalkyl acrylates and polyalkyl methacrylates.

9. The method of claim 3 wherein the polymer is selected from the group consisting of polymaleic anhydride, ethylene-maleic anhydride copolymer, styrene-maleic anhydride copolymer and mixtures thereof.

10. A solid polymeric composition comprising a polymer selected from the group consisting of homopolymers and copolymers of maleic anhydride said polymer having reacted thereto an arylmercurioxycarbonyl radical.

11. The composition of claim 10 wherein the arylmercurioxycarbonyl radical has the formula

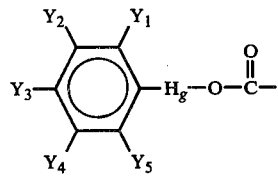

wherein the substituents $Y_1$ to $Y_5$ can be the same or different and are independently selected from the group consisting of hydrogen, fluorine, chlorine, bromine, iodine, alkyl containing 1-4 carbon atoms, alkoxy containing 1-4 carbon atoms, phenyl, nitro and alkylthio containing 1-4 carbon atoms.

12. The polymeric composition of claim 10 wherein the polymer is selected from the group consisting of polymaleic anhydride, ethylene-maleic anhydride copolymer, styrene-maleic anhydride copolymer and mixtures thereof.

13. A solid cross-linked polymeric composition comprising a polymer selected from the group consisting of homopolymers and copolymers of maleic anhydride and acrylic acid, methacrylic acid and esters thereof, said polymer having reacted thereto an arylmercurioxycarbonyl radical and an epoxy crosslinking agent.

14. The method of claim 4 wherein the aryl mercury compound is phenyl mercuric hydroxide.

15. The method of claim 4 wherein substituents $Y_1$ to $Y_5$ are all hydrogen.

16. The composition of claim 11 wherein the substituents $Y_1$ to $Y_5$ are all hydrogen.

17. The composition of claim 13 wherein said arylmercurioxycarbonyl radical is phenylmercurioxycarbonyl.

18. The composition of claim 13 wherein said epoxy crosslinking agent is diglycidyl ether of 2,2-bis(4'-hydroxyphenyl)propane.

* * * * *